United States Patent [19]

Bernat et al.

[11] Patent Number: 5,989,578
[45] Date of Patent: Nov. 23, 1999

[54] ASSOCIATIONS OF ACTIVE PRINCIPLES CONTAINING CLOPIDOGREL AND AN ANTITHROMBOTIC AGENT

[75] Inventors: André Bernat, Cugnaux; Jean Marc Herbert, Tournefeuille; Pierre Savi, Muret, all of France

[73] Assignee: Sanofi, Paris, France

[21] Appl. No.: 09/117,904

[22] PCT Filed: Feb. 17, 1997

[86] PCT No.: PCT/FR97/00296

§ 371 Date: Aug. 12, 1998

§ 102(e) Date: Aug. 12, 1998

[87] PCT Pub. No.: WO97/29753

PCT Pub. Date: Aug. 21, 1997

[30] Foreign Application Priority Data

Feb. 19, 1996 [FR] France ................................. 96 02027

[51] Int. Cl.⁶ ............................. A61F 13/00; A61F 9/02; A61K 9/64; A61K 9/20; A61K 9/14
[52] U.S. Cl. ........................ 424/422; 424/427; 424/434; 424/436; 424/456; 424/465; 424/489; 514/165; 514/301

[58] Field of Search ...................... 424/489, 422, 424/434, 427, 436, 456, 465; 514/165, 301

[56] References Cited

FOREIGN PATENT DOCUMENTS 2307538  11/1976  France .
2307538  12/1976  France .

OTHER PUBLICATIONS

Herbert, J.M. Clopidgorel and antiplatelet therapy. Expert Opinion Investigating Drugs. 1994. 3(5):449–455. XP 000610730.

Expert Opin. Invest. Drugs, 1994, 3/5 (449–455), United Kingdom, Herbert, J. M. Clopidogrel and antiplatelet therapy.

*Primary Examiner*—Thurman K. Page
*Assistant Examiner*—Alysia Berman
*Attorney, Agent, or Firm*—Michael D. Alexander

[57] ABSTRACT

The invention relates to a pharmaceutical composition containing an association of active principles, wherein the active principles are clopidogrel and aspirin, each constituent being present in a free form or in the form of a pharmaceutically acceptable salt.

25 Claims, No Drawings

ASSOCIATIONS OF ACTIVE PRINCIPLES CONTAINING CLOPIDOGREL AND AN ANTITHROMBOTIC AGENT

The subject of the present invention is a new combination of active ingredients with anti-platelet aggregation activity consisting of clopidogrel and aspirin, and pharmaceutical compositions containing them.

The active ingredients constituting the combination are present in the free state or in the form of one of their pharmacologically acceptable salts.

During the last decade, there has been a lot of interest in the study of the role played by the platelets in the development of diseases associated with atherosclerosis (myocardial infarction, angor, cerebral attack, peripheral arterial diseases and the like). The well-established role of the platelets in arterial thrombosis has allowed the development of numerous medicaments which inhibit the functions of the platelets and the discovery of the essential role of ADP in the thrombotic process has led to the development of ticlopidin, a potent antithrombotic agent. This thieno[3,2-c]pyridine derivative is described in Patent FR 73 03503. Ticlopidin selectively inhibits the platelet aggregation induced by ADP as well as that of other agonists, mediated by ADP [Féliste et al., Thromb. Res., 1987, 48, 403–415).

In multicentre double-blind clinical studies, ticlopidin proved to be significantly more effective than aspirin or a placebo in the prevention of cerebral attack in patients having a high risk of vascular accidents (Gent et al., Lancet, 1989, 8649, 1215–1220; Hass et al., N. Eng. J. Med., 1989, 321, 501–507). It also proved significantly more effective than the placebo in patients exhibiting a high risk of central or peripheral vascular accidents (Janzon et al., Scand. J. Int. Med., 1990, 227, 301–308).

Although it is known, to date, that aspirin and ticlopidin act via two different mechanisms of action, numerous studies have compared the efficacy of these two medicaments and it is only very recently that a few studies have suggested that ticlopidin, administered in combination with aspirin, could be of great interest in relation to acute thrombosis, as a replacement of current poorly effective treatments, in patients in whom a metallic endovascular prostheses had been implanted (Van Belle et al., Cor. Art. Dis., 1995, 6, 341–345).

The combination of ticlopidin and aspirin is claimed in patent FR 75 12084 for its use as anti-platelet aggregation agent endowed with a haemodynamic effect which is considerably qualitatively and quantitatively superior to that of ticlopidin alone. These results were demonstrated with the aid of pharmacological studies which related to the platelet aggregation inhibiting properties by making measurements of the platelet aggregation induced by ADP or collagen. The results which were obtained are predictive of a therapeutic importance of the ticlopidin-aspirin combination in some types of acute thrombosis following in particular some surgical operations but are not sufficient to deduce therefrom an indication in the secondary prevention of vascular accidents in atherometous disease or alternatively in endarterectomy or fitting of metallic endovascular prostheses.

It is moreover known that other combinations of anti-platelet aggregation agents, such as for example the combination aspirin-dipyridamole, have been the subject of clinical studies against dipyridamole alone or aspirin alone in the study of the prevention of cerebral vascular accident or of occlusion of the vascular shunt in patients. The conclusion of these studies was that the aspirin-dipyridamole combination does not possess any significant beneficial effect greater than that observed with dipyridamole alone or aspirin alone in the secondary prevention of cerebral atherothrombotic ischaemia or towards thrombosis (Acta. Neurol. Scand., 1987, 76(6), 413–421; Thrombosis, 1994, Alert No. 12; Thrombosis, 1994, Alert No. 9. Thrombosis, 1993, Alert No. 9; Thrombosis, 1993, Alert No. 2).

The fitting of metallic endovascular prostheses at the coronary and carotid level can be considered today as an important therapeutic advance in the prevention and treatment of central and peripheral vascular accidents. However, these prostheses exhibit a potent prothrombotic effect due to their metallic nature which it is essential today to prevent with the aid of antithrombotic agents and mainly anti-platelet aggregation agents.

Another thienopyridin derivative, clopidogrel described in EP 099 802 has also proved to be a potent antithrombotic, acting through a mechanism of action identical to that of ticlopidin (Savi et al., J. Pharmacol. Exp. Ther., 1994, 269, 772–777; Herbert et al., Cardiovasc. Drug Rev., 1993, 11, 180–198).

Its use could be beneficial in relation to pathological states such as disorders of the cardiovascular and cerebrovascular system such as the thromboembolic disorders associated with atherosclerosis or with diabetes such as unstable angina, cerebral attack, restenosis following angioplasty, endarterectomy or fitting of metallic endovascular prostheses, with rethrombosis following thrombolysis, with infarction, with dementia of ischaemic origin, with peripheral arterial diseases, with haemodialyses, with auricular fibrillations or during the use of vascular prostheses or aortocoronary bypasses or in relation to stable or unstable angor.

Clopidogrel is, depending on the aggregation agents used, in animals and in man about 10 to 50 times more effective than ticlopidin. Furthermore, unlike the latter, clopidogrel exhibits a practically immediate anti-aggregation activity which appears within 15 minutes after the administration whereas ticlopidin requires, in order to be effective, a prolonged administration of at least 3 days at much higher doses. Furthermore, unlike ticlopidin, clopidogrel can be administered by the intravenous route and exhibits, by this route, anti-aggregation effects which are completely equivalent to those obtained by the oral route (Herbert et al., Cardiovasc. Drug Rev., 1993, 11, 180–198). This is not the case for ticlopidin which can only be administered by the oral route.

Quite surprisingly and unexpectedly, the clopidogrel-aspirin combination of the invention proved to be endowed with a synergistic activity of the two active ingredients. This effect is characterized in relation to the aggregation of rabbit platelets with collagen, sole aggregation agent which can be used because of its joint dependency, by ADP and by the metabolism of arachidonic acid.

Furthermore, a similar synergistic effect was observed in relation to the formation of a thrombus of arterial origin induced by the implantation of a thrombogenic surface (silk thread) implanted in a catheter joining the carotid artery and the jugular vein of the rabbit.

The combinations according to the invention do not increase the haemorrhagic risk assessed by the extension of the bleeding time and are, moreover, not very toxic. Their toxicity is compatible with their use as medicament for the treatment of the disorders and of the diseases of thrombotic origin mentioned above.

The combinations according to the invention can be formulated in pharmaceutical compositions for administration to mammals, including man, for the treatment of the abovementioned diseases.

According to the invention, clopidogrel and aspirin can be administered in the form of a pharmaceutically acceptable salt.

These salts are those commonly used in pharmacy, such as acetate, benzoate, fumarate, maleate, citrate, tartrate, gentisate, methane sulphonate, ethane sulphonate, benzene sulphonate, lauryl sulphonate, dobesilate and paratoluene sulphonate.

In the text which follows, the quantities of clopidogrel and of aspirin are expressed as clopidogrel and aspirin equivalents in non-salified, free form.

Advantageously, the compositions of the invention comprise clopidogrel and aspirin in a molar ratio (aspirin/clopidogrel) of between 2.5 and 11.5, preferably between 5 and 9, better still between 7 and 8.

The combinations according to the invention can be used at daily doses of clopidogrel or of aspirin of 0.1 to 100 mg per kilo of body weight of the mammal to be treated.

In human beings, the dose may vary for each of the components from 1 to 500 mg per day, depending on the age of the subject to be treated and the type of treatment: prophylactic or curative.

In the pharmaceutical compositions of the present invention, the active ingredients are generally formulated in dosage units containing from 0.1 to 500 mg of the said active ingredient per unit dosage.

The subject of the present invention is therefore the pharmaceutical compositions which contain, as active ingredient, a combination of clopidogrel and aspirin. These compositions are preferably made so as to be administerable by the oral or parenteral route.

In the pharmaceutical compositions of the present invention for oral, sublingual, subcutaneous, intramuscular, intravenous, intradermal, local or rectal administration, the active ingredient may be administered in unit forms for administration, mixed with conventional pharmaceutical carriers, to animals and to human beings. The appropriate unit forms for administration comprise the forms for oral administration such as tablets, gelatin capsules, powders, granules and oral solutions or suspensions, the forms for sublingual or buccal administration, the forms for subcutaneous, intramuscular, intravenous, intranasal or intraocular administration and the forms for rectal administration.

When a solid composition in the form of tablets is prepared, the main active ingredient is mixed with a pharmaceutical vehicle such as gelatin, starch, lactose, magnesium stearate, talc, gum arabic and the like. The tablets can be coated with sucrose or other appropriate materials or alternatively they can be treated such that they have a prolonged or delayed activity and that they continuously liberate a predetermined quantity of active ingredient.

A preparation in the form of gelatin capsules is obtained by mixing the active ingredient with a diluent and by pouring the mixture obtained into soft or hard gelatin capsules.

A preparation in syrup or elixir form may contain the active ingredient together with a sweetener, preferably calorie free, methylparaben or propylparaben as antiseptic, as well as a taste enhancer and an appropriate colouring.

The water-dispersible granules or powders may contain the active ingredient mixed with dispersing agents or wetting agents, or suspending agents, such as polyvinylpyrrolidone, as well as sweeteners or flavour correctors.

For rectal administration, suppositories are used which are prepared with binders which melt at the rectal temperature, for example cocoa butter or polyethylene glycols.

For parenteral, intranasal or intraocular administration, aqueous suspensions, isotonic saline solutions, sterile and injectable solutions are used which contain dispersing agents and/or wetting agents which are pharmacoligically compatible, for example propylene glycol or butylene glycol.

The active ingredient can also be formulated in the form of microcapsules, optionally with one or more carriers or additives.

The active ingredients of the combinations can also be provided in the form of a complex with cyclodextrin, for example $\alpha$-, $\beta$- or $\gamma$-cyclodextrin, 2-hydroxypropyl-$\beta$-cyclodextrin or methyl-$\beta$-cyclodextrin.

When the compositions of the invention are administered in man by the parenteral or oral route, it is preferable that the daily dose of clopidogrel is between 50 and 100 mg, the daily dose of aspirin being between 100 and 500 mg.

It will be noted that according to the invention, clopidogrel and aspirin can both be administered by the oral route, or both by the parenteral route or one can be administered by the oral route (preferably aspirin) and the other by the parenteral route (preferably clopidogrel).

According to a preferred embodiment, the daily dose of clopidogrel administered in man by the parenteral and/or oral route is between 65 and 100 mg, better still between 65 and 85 mg, the daily dose of aspirin administered by the parenteral route being between 200 and 400 mg, better still between 315 and 335 mg.

Preferably, the dose of clopidogrel is in this case 75 mg per day and the dose of aspirin is 325 mg per day.

The combinations of active ingredients according to the invention have been the subject of pharmacological studies. Tests were carried out in relation to the test of aggregation of rabbit platelets with collagen as described above (Born et al., J. Physiol., 1963, 168, 178–95) . Briefly, 2.5 to 3 kg New Zealand rabbits were treated by the oral route with ticlopidin (100 mg/kg/d) for 3 days or by the intravenous route with clopidogrel (10 mg/kg). One hour after the last administration, the animals were treated by the intravenous route with aspirin (1 mg/kg).

Five minutes after the administration of aspirin, the animals were anaesthetized with ether and 2 ml of blood were collected from the median artery of the ear and mixed with 0.2 ml of a 3.8% solution of sodium citrate in water. The platelet-rich plasma was obtained by centrifugation of the blood at 500 g for 10 minutes at 15° C. The number of platelets was then adjusted to $10^6$ cells per $\mu$l with the aid of plasma low in platelets, obtained by centrifugation (3000 g, 15 min.) of anticoagulated blood.

The aggregation of the platelets was measured according to the method of Born (Born et al., J. Physiol., 1963, 168, 178–95) with the aid of a double canal aggregometer (Chrono Log) with stirring (900 rpm) at 37° C. The aggregation of the platelets was induced by collagen (12.5 $\mu$g/ml).

The antithrombotic effect of the clopidogrel or ticlopidin combination with aspirin was determined in relation to the formation of a thrombus on a silk thread present in an arteriovenous shunt implanted between the carotid artery and the jugular vein of the rabbit as described by Umetsu et al. (Thromb. Haemostas., 1978, 39, 74–83) . Briefly, 2.5 to 3 kg New Zealand rabbits were treated by the oral route with ticlopidin (100 mg/kg/d) for 3 days or by the intravenous route with clopidogrel (10 mg/kg).

The animals were anaesthetized by subcutaneous administration of sodium pentobarbital (30 mg/kg). Two polyethylene tubes 12 cm long (internal diameter: 0.6 mm; external diameter: 0.9 mm) attached by a central part 6 cm long (internal diameter: 0.9 mm) containing a silk thread 5 cm long were placed between the right carotid artery and the left jugular vein. One hour after the last administration of ticlopidin or of clopidogrel, the animals were treated by the intravenous route with aspirin (1 mg/kg). The central part of the shunt was then placed and then removed after 20 minutes of circulation of blood in the shunt. The weight of the thrombus present on the silk thread was then determined.

The results shown in TABLE 1 indicate that clopidogrel (10 mg/kg) or aspirin (1 mg/kg) administered by the intravenous route in a single dose in rabbit inhibit the aggregation of the platelets which is induced by collagen. Ticlopidin, administered by the oral route (100 mg/kg/d) for 3 days also exhibits a significant inhibitory effect in relation to the aggregation of the platelets with collagen.

In all cases, the joint administration of clopidogrel and aspirin resulted in a significant synergistic effect in relation to the aggregation of the platelets with collagen. That is to say that when the products were administered in combination, the anti-aggregation effect obtained was always greater than the mere sum of the effects of the two test products taken separately.

Compared with the mere additive effect observed between the anti-aggregation effect of ticlopidin and aspirin obtained and claimed in patent FR 73 03503, this activity is completely new and unexpected.

In the same manner, the antithrombotic activity of clopidogrel was potentiated by combination with aspirin. Under these conditions, and as in relation to the aggregation of the platelets with collagen, a significant synergistic effect was observed (TABLE 2).

TABLE 1

Effect of the products alone or in combination in relation to the aggregation of rabbit platelets with collagen.

| Active ingredients | Doses | % inhibition |
| --- | --- | --- |
| Ticlopidin | 100 mg/kg/D - 3 D | 35 ± 3% |
| Clopidogrel | 10 mg/kg | 42 ± 6% |
| Aspirin | 1 mg/kg | 21 ± 2% |
| Ticlopidin + Aspirin | 100 + 1 mg/kg | 52 ± 6% |
| Clopidogrel + Aspirin | 10 + 1 mg/kg | 98 ± 1% |

The values indicated in the table are the mean values on five experiments ± standard errors (n=5)

TABLE 2

Effect of the products alone or in combination in relation to the formation of an arterial thrombus on a silk thread implanted in an arteriovenous shunt in rabbit.

| Active ingredients | Doses | % inhibition |
| --- | --- | --- |
| Ticlopidin | 100 mg/kg/D - 3 D | 25 ± 9% |
| Clopidogrel | 10 mg/kg | 34 ± 4% |
| Aspirin | 1 mg/kg | 19 ± 5% |
| Ticlopidin + Aspirin | 100 + 1 mg/kg | 45 ± 3% |
| Clopidogrel + Aspirin | 10 + 1 mg/kg | 82 ± 1% |

The values indicated in the table are the mean values on five experiments ± standard errors (n=5)

We claim:

1. A pharmaceutical composition comprising a combination of clopidogrel aspirin, both constituents being present in the free state or in the form of a pharmaceutically acceptable salt.

2. A pharmaceutical composition according to claim 1, comprising clopidogrel and aspirin in combination with at least one pharmaceutical excipient.

3. A pharmaceutical composition according to claim 2 in a form administerable by the parenteral route or by the oral route.

4. A pharmaceutical composition according to claim 3 wherein clopidogrel and aspirin are present in an aspirin/clopidogrel molar ratio of between 2.5 and 11.5.

5. A pharmaceutical composition according to claim 1 for the treatment of a pathology induced by platelet aggregation.

6. A method for the treatment of a pathology induced by platelet aggregation, which comprises administering to a human in need of such treatment, a dose of 1 to 500 mg per day of clopidogrel and a dose of 1 to 500 mg per day of aspirin, the doses being expressed in equivalent quantity of clopidogrel and of aspirin in free form.

7. A method according to claim 6, in which the treatment involves the administration by the parenteral and/or oral route of 50 to 100 mg of clopidogrel per day and of 100 to 500 mg of aspirin per day.

8. A method according to claim 6, in which the treatment involves the administration by the parenteral and/or oral route of 65 to 100 mg of clopidogrel per day and of 200 to 400 mg of aspirin per day.

9. A method for the treatment of a pathology induced by platelet aggregation comprising the administration of an effective quantity of clopidogrel and, concomitantly, the administration of an effective quantity of aspirin, the clopidogrel and the aspirin being administered in the free state or in the form of a pharmaceutically acceptable salt.

10. A method according to claim 9, wherein the pathology induced by platelet aggregation is chosen from stable angor, unstable angor, disorders of the cardiovascular and cerebrovascular system, disorders associated with the use of vascular prostheses and disorders associated with aortocoronary bypasses.

11. A method according to claim 10, wherein the disorders of the cardiovascular and cerebrovascular system are chosen from thromboembolic disorders associated with atherosclerosis, with diabetes, with rethrombosis following thrombolysis, with infarction, with dementia of ischaemic origin, with peripheral arterial diseases, with haemodialysis and with auricular fibrillations.

12. A method according to claim 11, wherein the thromboembolic disorders associated with atherosclerosis and with diabetes are chosen from unstable angina, cerebral attack, restenosis following angioplasty, endarterectomy and the fitting of metallic endovascular prostheses.

13. A method according to claim 9, involving the administration in man of 1 to 500 mg per day of clopidogrel and of 1 to 500 mg per day of aspirin, the doses being expressed in equivalent quantity of clopidogrel and of aspirin in free form.

14. A method according to claim 9, involving the administration in man by the parenteral and/or oral route of 50 to 100 mg per day of clopidogrel and of 100 to 500 mg per day of aspirin, the doses being expressed in equivalent quantity of clopidogrel and of aspirin in free form.

15. A method according to claim 9, involving the administration in man by the parenteral and/or oral route of 65 to 100 mg per day of clopidogrel and of 200 to 400 mg per day of aspirin, the doses being expressed in equivalent quantity of clopidogrel and of aspirin in free form.

16. A method according to claim 15 involving the administration in man by the parenteral and/or oral route of 65 to 85 mg per day of clopidogrel and of 315 to 335 mg per day of aspirin, the doses being expressed in equivalent quantity of clopidogrel and of aspirin in free form.

17. A pharmaceutical composition according to claim 4 wherein clopidogrel and aspirin are present in an aspirin/clopidogrel molar ratio of between 5 and 9.

18. A pharmaceutical composition according to claim 2 for the treatment of a pathology induced by platelet aggregation.

19. A pharmaceutical composition according to claim 3 for the treatment of a pathology induced by platelet aggregation.

20. A pharmaceutical composition according to claim 4 for the treatment of a pathology induced by platelet aggregation.

21. A pharmaceutical composition according to claim 17 for the treatment of a pathology induced by platelet aggregation.

22. A method according to claim 8, in which the treatment involves the administration by the parenteral and/or oral route of 65 to 85 mg of clopidogrel per day and of 315 to 335 mg of aspirin per day.

23. A method according to claim 6 wherein the pathology induced by platelet aggregation is chosen from stable angor, unstable angor, disorders of the cardiovascular and cerebrovascular system, disorders associated with aortocoronary bypasses and disorders associated with the use of vascular prostheses.

24. A method according to claim 23, wherein the disorders of the cardiovascular and cerebrovascular system are chosen from thromboembolic disorders associated with atherosclerosis or diabetes, rethrombosis following thrombolysis, infarction, dementia of ischaemic origin, peripheral arterial diseases, haemodialyses and auricular fibrillations.

25. A method according to claim 24, wherein the thromboembolic disorders associated with atherosclerosis or diabetes are chosen from unstable angina, cerebral attack, restenosis following angioplasty, endarterectomy, and the fitting of metallic endovascular prostheses.

* * * * *